United States Patent [19]

Billig et al.

[11] 4,409,149

[45] Oct. 11, 1983

[54] PROCESS FOR PRODUCING CATALYST PRECURSORS

[75] Inventors: Ernst Billig, Charleston; David R. Bryant, South Charleston, both of W. Va.

[73] Assignee: Union Carbide Corporation, Danbury, Conn.

[21] Appl. No.: 278,897

[22] Filed: Jun. 29, 1981

[51] Int. Cl.$^3$ .............................................. C07F 15/00
[52] U.S. Cl. .................................................. 260/429 R
[58] Field of Search ....................................... 260/429 R

[56] References Cited

U.S. PATENT DOCUMENTS

| | | | |
|---|---|---|---|
| 3,511,880 | 9/1970 | Booth et al. | 260/604 |
| 3,527,809 | 9/1970 | Pruett et al. | 252/431 P X |
| 3,547,964 | 12/1970 | Olivier | 260/429 R |
| 3,646,079 | 2/1972 | Lawrenson | 260/429 J |
| 4,021,463 | 5/1977 | Kummer et al. | 260/429 R |
| 4,113,754 | 9/1978 | Kummer et al. | 260/429 R |

FOREIGN PATENT DOCUMENTS 670289 3/1966 Belgium .

OTHER PUBLICATIONS

Bonati et al., J. Chem. Soc. 3156 (1964).
J. Organometallic Chem. 43 425 (1972).

*Primary Examiner*—Helen M. S. Sneed
*Attorney, Agent, or Firm*—Reynold J. Finnegan

[57] ABSTRACT

This invention relates to a novel process for the preparation of rhodium(I) carbonyltriorganophosphorus mono-$\beta$-ketoenolate complexes which comprises reacting a halocarbonylbis(triorganophosphorus) rhodium(I) complex, a $\beta$-ketoenolate source and an oxygen transfer agent. The complexes so produced are useful as precursors for catalysts in hydroformylation processes.

16 Claims, No Drawings

PROCESS FOR PRODUCING CATALYST PRECURSORS

BACKGROUND OF THE INVENTION

This invention relates to a process for preparing rhodium(I) carbonyltriorganophosphorus mono-β-ketoenolate complexes from halocarbonylbis(triorganophosphorus) rhodium(I) complexes. Such complexes are useful as catalysts in hydroformylation processes. Hydroformylation is the general term applied to the reaction of an olefin with hydrogen and carbon monoxide to form an aldehyde.

U.S. Pat. No. 3,527,809 (Pruett, et al.) discloses an improved rhodium-catalyzed hydroformylation process which results in a high ratio of normal to branched-chain aldehydes. This process has proven very successful commercially. In this process certain rhodium complexes (i.e. catalyst precursors) are added to the reaction medium. For example, acetylacetonatodicarbonyl rhodium(I) (Rh(CO)$_2$acac) can be added to the reaction medium where it forms active catalyst. Another such catalyst precursor is acetylacetonatocarbonyl(triphenylphosphine) rhodium(I) complex (hereinafter referred to as "Complex I"). The basic hydroformylation process of Pruett, et al. has been further improved since its invention. Such further improvements include removing product aldehyde by recycling gas (U.S. Pat. No. 4,247,486), providing an alkyldiaryl phosphine ligand in the reaction medium (U.S. Pat. No. 4,260,828) and using the rhodium catalyst in a condensate solvent (U.S. Pat. No. 4,148,830).

It is known that the rhodium complex catalyst loses activity (i.e., becomes partially deactivated) during prolonged use in such hydroformylation processes. Because of the high cost of rhodium, several methods have been developed to maintain the level of activity of the catalyst and to reactivate deactivated catalyst.

U.S. patent application Ser. No. 120,101 filed Feb. 28, 1980, now U.S. Pat. No. 4,297,239 discloses a method of concentrating the spent hydroformylation reaction medium using a distillation technique in a wiped film evaporator. The resulting rhodium complex concentrate, especially when supplemented with a treatment by air, is an active catalyst precursor.

The rhodium complex concentrate may alternatively be treated according to the method disclosed in U.S. patent application Ser. No. 221,502, filed Dec. 30, 1980, now U.S. Pat. No. 4,363,764. This process entails treating the distilled rhodium complex concentrate with a halide ion source, a carbon monoxide source and free triorganophosphorus ligand, initially to prepare a halocarbonylbis(triorganophosphorus) rhodium(I) complex ("Complex II"). Ser. No. 221,502 further discloses that if Complex II is reacted with a metal hydride reducing agent and free triorganophosphorus ligand without isolating Complex II from its product mixture, the reaction process will form a hydridocarbonyltris(triorganophosphorus) rhodium(I) complex, which is useful as a hydroformylation catalyst precursor. Although Ser. No. 221,502 broadly discloses that Complex II is useful as source material for catalyst precursors, no process for producing a β-ketoenolate rhodium complex precursor is disclosed.

U.S. Pat. No. 4,021,463 discloses a process for preparing Complex II by treating the distillation residue of a hydroformylation mixture with an aqueous mineral acid and a peroxide to convert the rhodium into a water-soluble salt which passes into the aqueous phase, mixing the resulting aqueous salt solution with a solvent, tertiary phosphine and hydrohalic acid or metal halide and reacting the aqueous solution with carbon monoxide or a carbon monoxide donor. Said patent further discloses that the hydridocarbonyltris(triorganophosphine) rhodium(I) complex, an active catalyst precursor, can be produced by simultaneously subjecting the aqueous starting solution to hydrogenation conditions or by subjecting a solvent solution of the halo-containing compound together with additional phosphine to hydrogenation conditions.

U.S. Pat. No. 4,113,754 discloses a process for preparing chlorocarbonylbis(triorganophosphine) rhodium(I) complexes ("Complex IIA") by treating a distillation residue of a hydroformylation mixture with oxygen-containing mineral acids and peroxides to form an aqueous rhodium salt solution which is then treated with a cation exchanger. The complexed rhodium ions are then eluted with hydrochloric acid and the solution obtained is reacted in the presence of a water-soluble organic solvent, a tertiary phosphine and carbon monoxide to produce Complex IIA. The patent further discloses that if the latter reaction is carried out under hydrogenation conditions, hydridocarbonyltris(triorganophosphine) rhodium(I) is produced.

Various processes are known for producing rhodium(I) carbonyltriorganophosphorus mono-β-ketoenolate complexes. By way of illustration, "Dicarbonyl-β-diketonato and Related Complexes of Rhodium(I)," Bonati and Wilkinson, J. Chem. Soc. 3156 (1964), discloses a process involving the following reactions:

$$RhCl_3 + CO \rightarrow [Rh(CO)_2Cl]_2 \qquad (1)$$

$$[Rh(CO)_2Cl]_2 + CH_3COCH_2COCH_3 + BaCO_3 \rightarrow Rh(CO)_2acac(acac = CH_3COCHCOCH_3^-) \qquad (2)$$

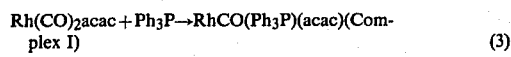

$$Rh(CO)_2acac + Ph_3P \rightarrow RhCO(Ph_3P)(acac)(Complex\ I) \qquad (3)$$

Japanese Pat. No. 75/53293 also discloses above Reaction (3). In addition, "Preparation and Reactivity of Some Halogen Bridged Complexes of Rhodium(I)," Barlex, Hacker and Kemmitt, J. of Organometallic Chemistry, 43 (1972) 425, discloses the following reaction for the preparation of Complex I:

$$Rh(PPh_3)_2acac + CO \rightarrow RhCO(PPh_3)(acac) + PPh_3 \qquad (4)$$

It also discloses the facile conversion of Complex I and analogous compounds to halocarbonyl(triorganophosphine) rhodium(I) complexes by reacting them with hydrogen halides.

Thus the prior art does not disclose a process for producing any rhodium(I) carbonyltriorganophosphorus mono-β-ketoenolate complex (e.g., Complex I) directly from a halocarbonylbis(triorganophosphorus) rhodium(I) complex (Complex II). The preparation of Complex I from RhCOCl(PPh$_3$)$_2$ can be represented hypothetically by Reaction (5) (displacement of chloride and triphenylphosphine from RhCOCl(PPh$_3$)$_2$ by acetylacetonate anion):

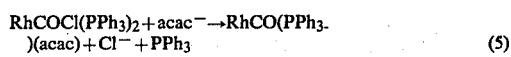

$$RhCOCl(PPh_3)_2 + acac^- \rightarrow RhCO(PPh_3)(acac) + Cl^- + PPh_3 \qquad (5)$$

However, while displacement reactions of coordinated chloride for the preparation of certain metal acetylacetonato derivatives are well known and are described in the prior art (see "Metal β-Diketonates and Allied Derivatives," Mehrota, et al., Academic Press, 1978, 18), it has now been found that Reaction (5) does not proceed or proceeds sluggishly to low conversions of Complex I (see Example 2 below). In fact, not only is RhCOCl(PPh3)2 a poor substrate for displacement of chloride by acetylacetonate anion, but it is well known that, with only a few exceptions, anionic displacement of chloride from RhCOCl(PPh3)2 proceeds poorly, if at all. Following known procedures for preparing anionic displacement products of RhCOCl(PPh3)2, the latter is first converted into RhCOF(PPh3)2 or RhCO(ClO4)(PPh3)2 [see "Fluoro Complexes of Rhodium(I) and Iridium(I)," Vaska and Peone, in *Inorganic Syntheses,* Parshall, editor, McGraw-Hill, 1974].

Various methods are known for oxidizing tertiary phosphines existing in free as well as coordinated states. However, there is no known method for preparing a rhodium(I) β-ketoenolate complex whereby the prior or simultaneous oxidation of a coordinated tertiary phosphine facilitates the substitution of a coordinated halide by β-ketoenolate to form said β-ketoenolate complex. The various known methods for oxidizing tertiary phosphines (free and coordinated) are illustrated by the following references.

"Tertiary Phosphine Oxides" (Hays and Peterson), which appears as Chapter 6 in *Organic Phosphorus Compounds,* Vol. 3 (Kosolapoff and Maier) discloses a method of oxidizing free tertiary phosphines to make phosphine oxides using a variety of oxidizing agents, including oxygen, peroxy compounds, olefin epoxides, nitrogen oxides, sulfur oxides and standard inorganic oxidants. Hays et al. also specifically discloses the use of t-butyl hydroperoxide for oxidizing free tertiary phosphines.

A literature and patent survey entitled "Tertiary Phosphines as Catalysts" (M. K. Moran, M & T Chemicals, Inc., 1975) discloses methods of oxidizing free trialkylphosphines using nitric acid, aqueous potassium permanganate, hydrogen peroxide, ferric chloride, olefin epoxides, and cyclic carbonates to produce trialkylphosphine oxides.

"In situ High Pressure, High-temperature Spectrophotometric Studies of the Chlorocarbonylbis(triphenylphosphine)rhodium(I) Hydroformylation Catalyst Activated by Hydroperoxides," Tinker and Morris, J. Organometallic Chem. 52, 1973, C55, teaches, among other things, that in the presence of one equivalent of an organic hydroperoxide (cyclohexenyl hydroperoxide) and under hydroformylation conditions, RhCOCl(PPh3)2 is converted into cis-Rh(CO)2ClPPH3:

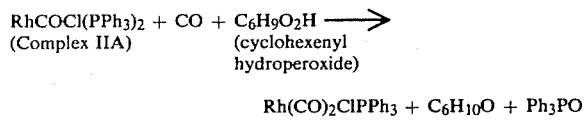

RhCOCl(PPh3)2 + CO + C6H9O2H ⟶
(Complex IIA)    (cyclohexenyl hydroperoxide)

Rh(CO)2ClPPh3 + C6H10O + Ph3PO

This is a substitution process of Complex (IIA) facilitated by oxygen transfer where the neutral triphenylphosphine ligand undergoing substitution (and oxidation) is being substituted by another neutral ligand, CO. It is not obvious from this, however, that in the presence of an oxygen transfer agent and an anionic ligand that substitution of the chloride in Complex (IIA) will occur to yield Complex (I):

RhCOCl(PPh3)2+acac⁻+RO2H→RhCO(PPh3)acac+Ph3PO  (Complex I)

Trimethylamine N-oxide has been employed extensively and exclusively to promote the substitution of coordinated CO in metal carbonyls by other neutral ligands including tertiary phosphines via prior or simultaneous oxidation of the coordinated CO (Blumer, Barnett, and Brown, J. Organometallic Chem., 173, (1979), 71–76, and references cited therein). However, none of these references discloses or suggests the use of trimethylamine N-oxide in the context of the present invention, namely, promoting substitution of a coordinated anion in a metal carbonyl by first or simultaneously oxidizing a coordinated tertiary phosphine ligand.

Thus, it is an object of this invention to provide a process for preparing rhodium(I) carbonyltriorganophosphorus mono-β-ketoenolate complexes from halocarbonylbis(triorganophosphorus) rhodium(I) complexes.

It is a further object of this invention to provide a process for preparing hydroformylation catalyst precursors.

It is still a further object of this invention to convert halocarbonylbis(triorganophosphorus) rhodium(I) complexes directly to rhodium(I) carbonyltriorganophosphorus mono-β-ketoenolate complexes.

SUMMARY OF THE INVENTION

It has now been discovered that rhodium(I) carbonyltriorganophosphorus mono-β-ketoenolate complexes which may be used as catalyst precursors for hydroformylation processes (particularly the Pruett, et al. process) can be prepared by reacting a halocarbonylbis(triorganophosphorus) rhodium(I) complex, a β-ketoenolate source and an oxygen transfer agent.

DESCRIPTION OF THE INVENTION

The present invention comprises reacting a halocarbonylbis(triorganophosphorus) rhodium(I) complex, a β-ketoenolate source and an oxygen transfer agent to form a rhodium(I) carbonyltriorganophosphorus mono-β-ketoenolate complex.

The starting material, a halocarbonylbis(triorganophosphorus) rhodium(I) complex, is conveniently derived from a rhodium complex concentrate generated from spent hydroformylation reaction medium. Such rhodium complex concentrates can be produced by any conventional method or combination of methods which result in a rhodium complex concentrate consisting essentially of from about 0.1 to about 30 percent by weight of a spent hydroformylation reaction medium having been produced by a process comprising concentrating a spent hydroformylation reaction medium so as to remove, while retaining a major amount of the rhodium values of the partially deactivated rhodium complex catalyst present in said medium, at least essentially all of the aldehyde products present in said medium, at least 50 percent by weight of the higher boiling aldehyde condensation by-products present in said medium having a boiling point below that of the free triorganophosphorus ligand present in said medium, and at least 50 percent by weight of the free triorganophosphorus ligand being present in said medium.

For example, it is generally preferred to concentrate the spent hydroformylation reaction medium by means of distillation as taught in U.S. application Ser. No. 120,101, filed Feb. 28, 1980, (Bryant, et al.), the entire disclosure of which is incorporated herein by reference thereto. Such a procedure involves concentrating the spent hydroformylation reaction medium into at least two material streams by means of distillation at temperatures of about 20° to about 350° C. and at pressures of about 1000 to about $1 \times 10^{-6}$ mm. Hg., wherein one stream is said rhodium complex concentrate (i.e. the distillation residue) containing a major amount of the rhodium values of the partially deactivated rhodium hydroformylation catalyst present in said medium.

The distillation procedure of Bryant et al. preferably takes place in two stages, the first stage being conducted at temperatures of about 20° to 250° C., preferably from 20° to 190° C., and pressures of about 1000 to about 0.1 mm Hg., preferably about 150 to 0.5 mm Hg., which may effect up to about a three-fold concentration of the spent hydroformylation reaction medium; the second stage of the distillation being conducted at temperatures of about 25° to 350° C., preferably from about 150° to about 300° C., and pressures of about 100 to $1 \times 10^{-6}$ mm Hg., preferably about 20 to 0.1 mm Hg., so as to further concentrate the bottom or residue product of the first stage to the finally desired rhodium complex concentrate which may contain from about 1000 to about 70,000 ppm, more preferably from about 1500 to about 15,000 ppm, and most preferably from about 2,000 to 12,000 ppm, of rhodium calculated as free metal.

The first distillation stage of Bryant et al. is employed to distill off and remove the most volatile components, e.g. the aldehyde products, that are present in the spent hydroformylation medium since such low boiling volatile components interfere with obtaining the desired low pressures employed in the second distillation stage and needed for the most effective removal of the less volatile (i.e. higher boiling) component and said free triorganophosphorus ligand present in said medium.

The second distillation stage of Bryant et al. involves taking the liquid residue or bottoms of said first distillation stage containing the partially deactivated rhodium complex catalyst and less volatile components, such as said higher boiling aldehyde condensation by-products and the free triorganophosphorus ligands of the spent hydroformylation reaction medium, and subjecting it to further distillation at the reduced pressures given above so as to distill off and remove free triorganophosphorus ligand and the higher boiling aldehyde condensation by-products that have a boiling point above said aldehyde products but below that of the free triorganophosphorus ligand present in said residue. The desired rhodium complex concentrate employable in this invention is thus recovered as the distillation residue of said second stage distillation and contains a major amount of the rhodium values of said partially deactivated catalyst (i.e., more than 50 percent by weight, preferably more than 90 percent by weight, of the total amount of rhodium values of said catalyst). For obvious economic reasons it is most desirable that the rhodium complex concentrate contain essentially (i.e., greater than 97 percent by weight) of all of the rhodium values of said partially deactivated catalyst.

The distillation of each separation stage of Bryant et al. can be carried out by using any suitable distillation system and can take place on a continuous and/or discontinuous (batch) basis. However, care should be taken to avoid overheating the rhodium complex. It is also important to maintain a high vacuum in the second distillation stage so that the temperature required for concentration can be minimized. Thus the distillation is preferably carried out at the lowest temperature and shortest residence time required to achieve the desired rhodium concentration. Accordingly it is preferred to employ a thin-film evaporator, such as a wiped-film evaporator, since in such systems residence times at elevated temperatures of less than 10 minutes should be suitable in most instances, and preferably such residence times will be less than about three minutes, whereas in a kettle-type batch distillation the residence time for the second stage of distillation can be hours. However, batch systems are readily suitable for the first stage of distillation, since such is concerned with only removing the most volatile (lower boiling) components of the spent medium and thus the distillation can be carried out at rather mild temperatures and at much higher pressures than those pressures employed in the second distillation stage. In general, it is preferred to carry out both distillation stages in a thin-film evaporator, especially a wiped-film evaporator. Such evaporators are well known in the art and thus need not be further discussed herein. Of course, it is also to be understood that the procedure of each distillation stage can be carried out more than once, i.e., repeated until the desired amount of volatiles have been removed and/or the desired rhodium concentration obtained.

It should be noted that a fundamental change in the rhodium species present in the partially deactivated catalyst occurs during the distillation concentrating procedure of Bryant et al. The rhodium species found in the rhodium complex concentrates produced by the distillation concentration procedure are different in that they are generally larger in size than those species found in partially deactivated rhodium complex catalysts. Said rhodium complex concentrates so obtained have a dark brownish color and are highly viscous rhodium complex mediums.

The halocarbonylbis(triorganophosphorus) rhodium(I) complexes which serve as starting materials for the process of this invention can be formed from rhodium complex concentrates obtained by any convenient means. A preferred method by which these materials may be obtained is that of U.S. patent application Ser. No. 221,502, filed Dec. 30, 1980, (Billig, et al.), the entire disclosure of which is hereby incorporated by reference thereto. According to the procedure disclosed therein, rhodium complex concentrate is reacted, in an essentially non-aqueous homogeneous organic reaction solution, with a halide ion source, a carbon monoxide source, and free triorganophosphorus ligand. The rhodium complex concentrate is first exposed to an oxidant such as oxygen and/or an organic peroxide, preferably in the form of an admixture of oxygen gas with an inert gas in a convenient manner. Any suitable halide ion source may be employed which will furnish the halogen radical of the desired halocarbonylbis(triorganophosphorus) rhodium(I) product. Such halogen radicals include, of course, chlorine, bromine, iodine and fluorine with chlorine being preferred. Illustrative sources of such halide ions include halogens, hydrohalic acids, halide salts e.g., alkali metal halides and the like; for instance, hydrochloric acid, hydrobromic acid, hydroiodic acid, sodium chloride, sodium bromide, and the like. The preferred source of halide ion is a hydrohalic acid especially hydrochloric acid. The source of halide ion need only be employed in an amount sufficient to provide at least that stoichiometric amount of halogen ion necessary to form the desired halocarbonylbis(triorganophosphorus) rhodium(I) product, i.e., at least one mole equivalent of halogen per mole of rhodium calculated as free metal in the rhodium complex concentrate starting material. Any suitable carbon monoxide source, as an alternative to carbon monoxide gas per se, may be employed in the method of Billig et al. which will furnish the carbonyl radical of the desired halocarbonylbis(triorganophosphorus) rhodium(I) product. In general, it is preferred to employ a source of carbon monoxide rather than carbon monoxide gas per se. The preferred source of carbon monoxide are high boiling amides, especially N,N-dimethylformamide, since such has been found to not only serve as a source of carbon monoxide, but also as an excellent solvent and/or compatibilizing agent for rendering the preferred hydrochloric acid and triphenylphosphine components of the Billig et al. process completely homogeneous with the rhodium complex concentrate employed in that process. The source of carbon monoxide need only be employed in an amount sufficient to provide at least that stoichiometric amount of carbon monoxide necessary to form the desired halocarbonylbis(triorganophosphorus) rhodium(I) product, i.e., at least one mole equivalent of carbon monoxide per mole of rhodium calculated as free metal in the rhodium complex starting material.

A free triorganophosphorus ligand (i.e., ligand that is not complexed with or tied to the rhodium of the partially deactivated rhodium complex catalyst) is also used in the method of Billig et al. Any suitable free triorganophosphorus ligand may be employed to furnish the triorganophosphorus radicals of the desired halocarbonylbis(triorganophosphorus) rhodium(I) complex. Obviously the choice of such phosphorus ligands will merely depend upon the nature of the rhodium complex product desired. Such phosphorus ligands are well known and include those already discussed above. For example in general, the preferred phosphorus ligands are those which have been heretofore employed as rhodium ligands in the hydroformylation field, e.g., as seen by U.S. Pat. No. 3,527,809. The amount of free triorganophosphorus ligand employed need only be at least that stoichiometric amount necessary to form the desired halocarbonylbis(triorganophosphorus) rhodium(I) product, i.e., at least two mole equivalents of free triorganophosphorus ligand per mole of rhodium calculated as free metal in the rhodium complex concentate starting material.

There are several β-ketoenolate sources that may be used in accordance with the present invention. Typical of such sources are those represented by the formula:

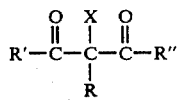

wherein R' is an alkyl or aryl group, R" is an alkyl, aryl, alkoxy or aryloxy group, R is hydrogen or an alkyl or aryl group and X is hydrogen, an alkali metal, ammonium or thallium(I). R,R' and R" each have preferably no more than 20 carbon atoms. Other typical sources include alkaline earth metal β-ketoenolates. It is preferable to employ a β-ketoenolate salt, such as sodium acetylacetonate. However, a β-ketoenolate salt precursor such as acetylacetone or ethyl acetylacetonate may be used with a base such as an alkali metal or alkaline earth metal hydroxide (e.g. sodium hydroxide). The amount of β-ketoenolate source employed in the process of this invention is at least one mole equivalent, preferably at least six mole equivalents, per mole equivalent of halocarbonylbis(triorganophosphorus) rhodium(I) complex.

There are several oxygen transfer agents which are effective in the process of this invention. Most preferred oxygen transfer agents are tert-butyl hydroperoxide, trimethylamine oxide, propylene oxide and styrene oxide. Also useful in this capacity are oxygen and cyclic carbonates. The oxygen transfer agent is preferably added in a quantity equal to or slightly in excess of one mole equivalent per mole equivalent of the halocarbonylbis(triorganophosphorus) rhodium(I) complex. When tert-butyl hydroperoxide is the oxygen transfer agent, an amount only slightly exceeding one mole equivalent per equivalent of the complex is preferable so as to preserve the selectivity of the oxidation-substitution reaction. If a larger amount is used, it is possible that more than one organophosphorus ligand may be oxidized or the rhodium(I) may be oxidized to yield a less desirable rhodium(III) complex. When propylene oxide or styrene oxide is employed as oxygen transfer agent, the excess amount is less critical, and an amount much greater than one mole equivalent per mole of the rhodium(I) complex reactant may be added to the reaction because these compounds are milder oxygen transfer agents than tert-butyl hydroperoxide and trimethylamine oxide. Trimethylamine oxide, as oxygen transfer agent, is preferably added in amounts in excess of one mole equivalent, more preferably at least 1.5 mole equivalents, per mole of halocarbonylbis(triorganophosphorus) rhodium(I) complex.

The reaction involved in the process of this invention is preferably conducted in an organic solvent such as an alcohol, amide, ester or ketone. More preferably, the solvent is acetone. There are no narrowly critical temperature or pressure limitations which bear on the practice of this invention, however, the desired selectivity tends to decrease at higher temperatures. A preferred temperature range for conducting the process of this invention is between 50° and 100° C.

By-products formed by the process of this invention include triorganophosphorus oxides and halogen-containing compounds. The particular by-products depend upon the reactants used. For example, when sodium acetylacetonate is used, the halogen-containing by-product is a sodium halide. When acetylacetone is used, an olefin oxide such as free propylene oxide can be used as both an oxygen transfer agent and a base (halide acceptor). This obviates the need for extensive water-washing to remove inorganic impurities. The by-products are readily separated from the desired reaction products by washing with suitable solvents.

The process of this invention provides a high-yield method of producing hydroformylation catalyst precursors in the form of β-ketoenolate rhodium(I) complexes. Yields of at least 34% and as high as 99% of rhodium recovered as β-ketoenolate rhodium(I) complexes from halocarbonylbis(triorganophosphorus) rhodium(I) complexes have been obtained using the process of this invention. When Complex I produced according to the process of this invention was used as catalyst precursor in a hydroformylation process, a reaction rate was achieved equal to that using conventionally prepared Complex I.

The following Examples are illustrative of the practice of this invention. However, they do not serve to limit the invention to the embodiments in the Examples.

As used in the Examples appearing below the following abbreviations and symbols have the indicated meanings:

| | |
|---|---|
| g | grams |
| Ph | phenyl |
| mmoles | millimoles |
| acac | $[CH_3COCHCOCH_3]^-$ |

EXAMPLE 1

Preparation of Rh(acac)COPPh$_3$ (Complex I) from RhClCO(PPh$_3$)$_2$ using tert-butyl hydroperoxide (TBHP)

To a stirred suspension of 2.0 g (2.9 mmoles) of RhClCO(PPh$_3$)$_2$ and 2.8 g (17.7 mmoles) of sodium acetylacetonate dihydrate, 0.35 g (2.7 mmoles) of 70% aqueous TBHP was added. The suspension was refluxed for 18 hours, then poured onto ice. A crude solid product weighing 1.4 g was isolated by filtration. The product was identified as Complex I by thin layer chromatography and infrared spectroscopy ($\Xi_{co} = 1980$ cm$^{-1}$). The rhodium content of the filtrate was evaluated and found to be 0.0128 g, or 4.3% of the rhodium originally charged. Thus, 95.7% of the RhClCO(PPh$_3$)$_2$ originally charged was converted to Complex I.

EXAMPLE 2

Attempted Preparation of Complex I from RhClCO(PPh$_3$)$_2$ without the use of TBHP The procedure of Example 1 was followed except that no TBHP was added to the suspension of RhClCO(PPh$_3$)$_2$ and sodium acetylacetonate dihydrate in acetone. The crude yellow solids weighing 1.98 g recovered by filtration were identified by infrared spectroscopy ($\nu_{co} = 1960$ cm$^{-1}$) and thin layer chromatography as unchanged RhClCO(PPh$_3$)$_2$.

EXAMPLE 3

Preparation of Complex I from Spent Hydroformylation Catalyst Wiped Film Evaporator (WFE) Residue using TBHP Using the procedure of Bryant, et al., a sample of spent hydroformylation catalyst was converted to a WFE residue which was used to prepare 67.0 g of RhClCO(PPh$_3$)$_2$ containing 9.98 g (97 mmoles) of rhodium. The RhClCO(PPh$_3$)$_2$ and 91 g (580 mmoles) of sodium acetylacetonate dihydrate were suspended in acetone. 12.8 g (100 mmoles) of 70% aqueous TBHP was added, and the suspension was refluxed for 6½ hours. The suspension was then poured onto ice, filtered and washed with distilled water. The recovered solids were then dried. The solids were identified by infrared spectroscopy as Complex I ($\nu_{co} = 1980$ cm$^{-1}$). The filtrate was analyzed for rhodium and found to contain 15% of that initially present corresponding to an 85% recovery in the form of Complex I.

EXAMPLE 4

Preparation of Complex I from RhClCO(PPh$_3$)$_2$ using Propylene Oxide

To a suspension of 2.0 g (2.9 mmoles) of RhClCO(PPh$_3$)$_2$ and 2.8 g (17.7 mmoles) of sodium acetylacetonate dihydrate in 100 ml of acetone was added 3.4 g (58 mmoles) of propylene oxide. The suspension was placed in a pressure bottle under 30 psi of nitrogen, heated to 65° C. and stirred for 19 hours. The suspension was filtered and 3 g of crude yellow solids were recovered. The filtrate was analyzed to determine rhodium content, and the solids were analyzed by infrared spectroscopy to determine their composition. It was found that the solids contained Complex I in an amount corresponding to 54% of the RhClCO(PPh$_3$)$_2$ originally charged.

EXAMPLE 5

Preparation of Complex I from RhClCO(PPh$_3$)$_2$ using Styrene Oxide

The procedure described in Example 4 was used, but 7.0 g (59.8 mmoles) of styrene oxide was used in place of propylene oxide as the oxygen-transfer agent. 55% of the rhodium in the original sample was recovered as Complex I as determined by filtrate analysis and infrared spectroscopic examination of the isolated solids.

EXAMPLE 6

Preparation of Complex I from RhClCO(PPh$_3$)$_2$ by Use of Acetylacetone and Propylene Oxide as Oxygen-Transfer Agent and Base (Halide Acceptor)

To a suspension of 2.0 g (2.9 mmoles) of RhClCO(PPh$_3$)$_2$ in acetone was added 1.74 g (17.4 mmoles) of acetylacetone and 3.4 g (58 mmoles) of propylene oxide. The reaction mixture was heated for 67 hours. Complex I was isolated as in Example 1. 34% of the original RhClCO(PPh$_3$)$_2$ was recovered as Complex I.

EXAMPLE 7

Preparation of Complex I from RhClCO(PPh$_3$)$_2$ using Trimethylamine Oxide (TMAO)

To a suspension of 2.0 g (2.9 mmoles) of RhClCO(PPh$_3$)$_2$ and 2.8 g (17.7 mmoles) of sodium acetylacetonate dihydrate in acetone was added 0.52 g (4.64 mmoles) of TMAO. The suspension was refluxed for 15½ hours and then filtered. The isolated crude solids were analyzed as in Example 1 to determine composition and the filtrate analyzed for rhodium concentration. 99% of the original RhClCO(PPh$_3$)$_2$ was converted to Complex I.

EXAMPLE 8

Preparation of Complex I from Spent Hydroformylation Catalyst WFE Residue using TMAO Using the procedure of Bryant, et al., a sample of spent hydroformylation catalyst was converted to a WFE residue which was used to prepare a 50.2 g (72.7 mmoles) sample of crude RhClCO(PPh$_3$)$_2$. The crude RhClCO(PPh$_3$)$_2$ was suspended in one liter of acetone along with 69 g (436 mmoles) of sodium acetylacetonate and 13.3 g (119 mmoles) of TMAO. This suspension was refluxed for 19 hours. Analysis of the filtrate and crude solids showed that 72% of the original RhClCO(PPh₃)₂ was converted to Complex I.

What is claimed is:

1. A process for preparing rhodium (I) carbonyltriorganophosphorus mono-β-ketoenolate complexes which comprises reacting (a) a halocarbonylbis(triorganophosphorus) rhodium (I) complex, (b) a β-ketoenolate source, and (c) an oxygen transfer agent, wherein the amount of β-ketoenolate source employed is at least one mole equivalent per mole equivalent of the halocarbonylbis(triorganophosphorus) rhodium (I) complex and wherein the oxygen transfer agent is present in a quantity equal to or exceeding one mole equivalent per mole equivalent of the halocarbonylbis(triorganophosphorus) rhodium (I) complex.

2. A process in accordance with claim 1 wherein said rhodium(I) carbonyltriorganophosphorus mono-β-ketoenolate complex of rhodium(I) is rhodium(I) carbonyl(triphenylphosphine) acetylacetonate.

3. A process in accordance with claim 1 wherein said halocarbonylbis(triorganophosphorus) rhodium(I) complex is a halocarbonylbis(triarylphosphine) rhodium(I) complex.

4. A process in accordance with claim 1 wherein said halocarbonylbis(triorganophosphorus) rhodium(I) complex is chlorocarbonylbis(triphenylphosphine) rhodium(I).

5. A process in accordance with claim 1 wherein said β-ketoenolate source is sodium acetylacetonate.

6. A process in accordance with claim 1 wherein said β-ketoenolate source is a β-diketone and a base.

7. A process in accordance with claim 1 wherein said β-ketoenolate source is acetylacetone.

8. A process in accordance with claim 1 wherein said oxygen transfer agent is selected from the group consisting of tert-butyl hydroperoxide, trimethylamine oxide, propylene oxide, styrene oxide or oxygen.

9. A process in accordance with claim 1 wherein said oxygen transfer agent is tert-butyl hydroperoxide.

10. A process in accordance with claim 1 wherein said oxygen transfer agent is trimethylamine oxide.

11. A process in accordance with claim 1 wherein said oxygen transfer agent is propylene oxide.

12. A process in accordance with claim 1 wherein said oxygen transfer agent is styrene oxide.

13. A process in accordance with claim 1 wherein tert-butyl hydroperoxide is the oxygen transfer agent and is present in quantities only slightly exceeding one mole equivalent per equivalent of said halocarbonylbis(triorganophosphorus) rhodium(I) complex.

14. A process in accordance with claim 1 wherein said oxygen transfer agent is an olefin oxide.

15. A process in according to claim 1 wherein said β-ketoenolate source is represented by the formula:

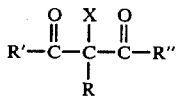

wherein R' is an alkyl or aryl group, R" is an alkyl, aryl, alkoxy or aryloxy group, R is hydrogen or an alkyl or aryl group and X is hydrogen, an alkali metal, ammonium or thallium(I).

16. A process according to claim 1 wherein said β-ketoenolate source is an alkaline earth metal β-ketoenolate.

* * * * *